United States Patent [19]

Woien

[11] 4,021,863
[45] May 10, 1977

[54] HEART VALVE PROSTHESIS
[75] Inventor: Arne Wøien, Lierbyen, Norway
[73] Assignee: M-K-V Corporation, Minneapolis, Minn.
[22] Filed: Sept. 13, 1976
[21] Appl. No.: 722,580
[52] U.S. Cl. .................................. 3/1.5; 137/527; 137/527.8
[51] Int. Cl.² .......................................... A61F 1/22
[58] Field of Search ......... 3/1.5, 1; 137/527, 527.4, 137/527.8

[56] References Cited
UNITED STATES PATENTS

| | | | |
|---|---|---|---|
| 3,476,143 | 11/1969 | Kaster | 3/1.5 X |
| 3,824,629 | 7/1974 | Shiley | 3/1.5 |
| 3,825,957 | 7/1974 | Kaster | 3/1.5 |
| 3,835,475 | 9/1974 | Child | 3/1.5 |
| 3,959,827 | 6/1976 | Kaster | 3/1.5 |

Primary Examiner—Ronald L. Frinks
Attorney, Agent, or Firm—Schroeder, Siegfried, Ryan & Vidas

[57] ABSTRACT

A heart valve having an annular base and a free-floating pivoting disc which alternately closes the annulus and is moved by blood flow pressure to an angularly open and positionally displaced orientation. A disc guide strut extending through a central opening in the disc generally directs and controls the movement of the disc from the open to closed position. A single outflow pivot is provided in planar alignment with the disc guide strut, and this pivot coupled with the absence of a wedging position for the disc minimizes the tendency to produce areas of blood stagnation.

6 Claims, 6 Drawing Figures

HEART VALVE PROSTHESIS

The use of heart valve prostheses to replace damaged and malfunctioning valves is well established. A large number of heart valve designs have been proposed and used. A similar design in certain respects to that of the present invention is shown in U.S. Pat. No. 3,959,827, which patent discusses the prior art in some detail. Despite the considerable efforts expended in design of heart valves, certain problems remain in those presently in use.

The present invention is to a heart valve having a design that overcomes or at least reduces certain of the disadvantages of the prior art valves. Among the advantages of the present valve are a lessened tendency to produce stagnation areas, a greater freedom of flow through the valve orifice and a reduced tendency for wear of the central disc and its pivots.

The invention will be described in greater particularity with reference to the accompanying drawings, wherein:

IN THE DRAWINGS

In the several figures of the drawings, like parts will be given the same numerical designation.

Figure 1:
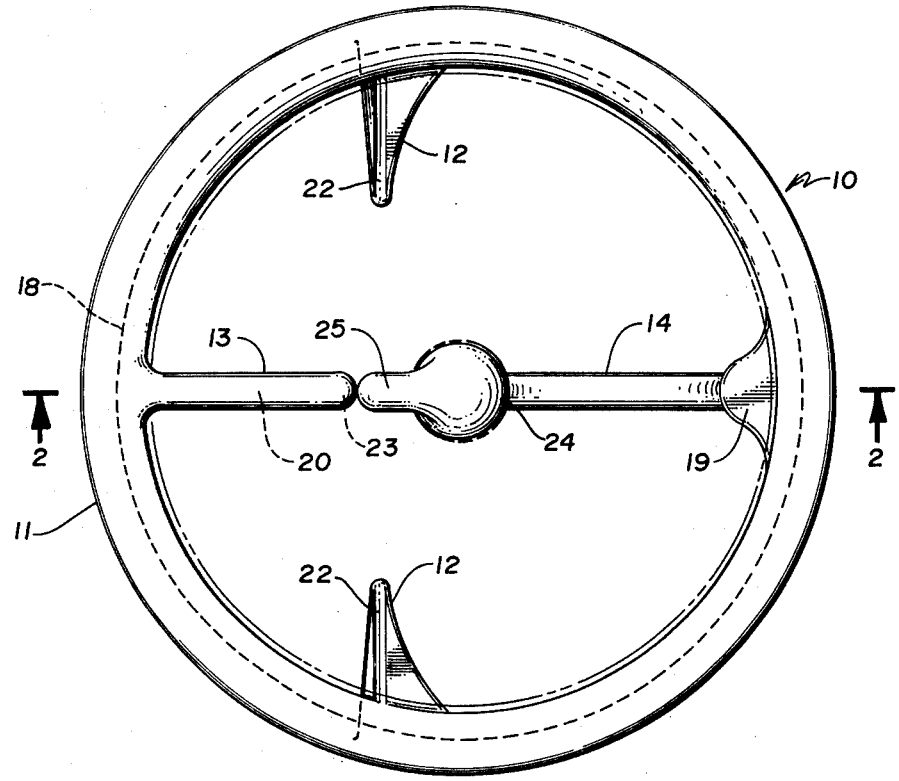
FIG. 1 is a top elevational view of a heart valve in accordance with the invention with the central disc omitted for purposes of clarity in the drawings.

Referring first to FIG. 1, there is illustrated in top elevational view a heart valve in accordance with the present invention. As noted, for purposes of clarity in the drawings, the valve disc had been omitted in this figure so as to show the several parts more clearly. All parts excepting the valve disc are metallic and may be made of stainless steel or titanium as is known in the art.

10 generally indicates a valve housing member which includes an annular valve base 11 which provides support for a pair of integral inflow pivots 12. Pivots 12 are identical to one another except for being mirror images and are positioned along a chordal axis of the interior periphery of the valve base 11 as seen in the drawings. The outer portions of the valve base 11 are shaped so as to provide a rim for holding of a sewing ring in the manner well known in the art. As the sewing ring feature is common to those of the prior art, it will not be discussed further herein.

Figure 3:
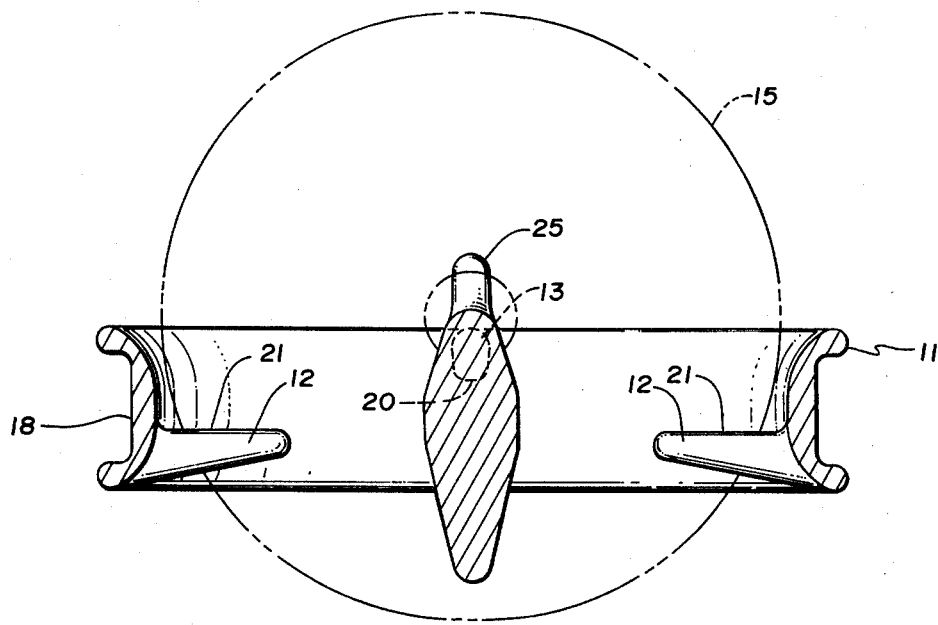
FIG. 3 is a sectional view along lines 3—3 of FIG. 1.
Figure 4:
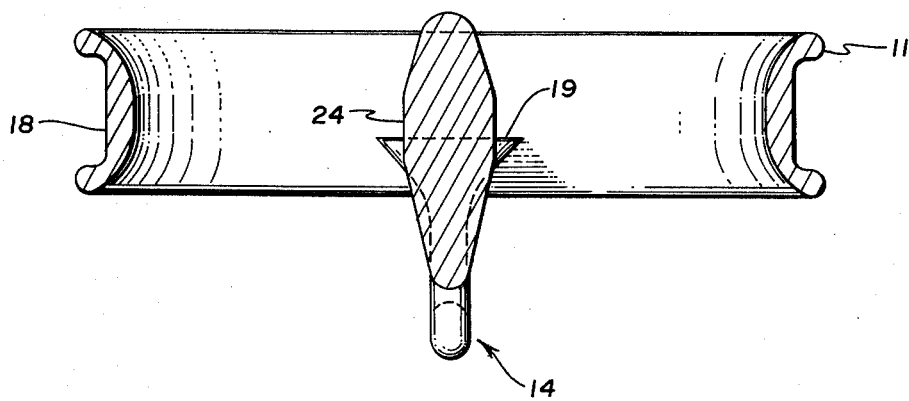
FIG. 4 is a sectional view along lines 4—4 of FIG. 1.
Figure 5:
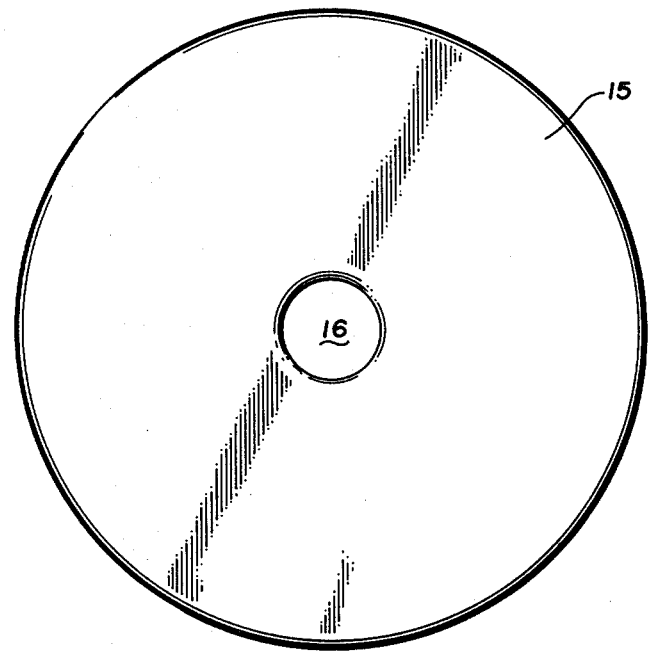
FIGS. 5 and 5a are front elevational and side views, respectively, of the disc used in cooperation with the apparatus of the invention.
Figure 5A:
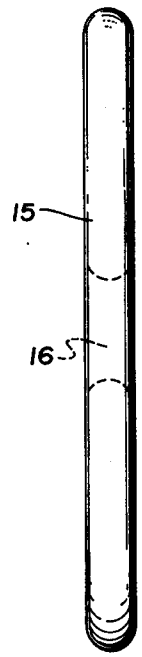

Extending transversely to the chordal axis of inflow pivots 12 and radially toward the center of annular member 11 is an outflow pivot 13 which cooperates with a disc guide strut 14 to guide the disc member 15 during the opening and closing operation of the valve. Members 13 and the operational portions of 14 are on planar alignment with one another at right angles to both the chord of pivots 12 and to the axis of the opening defined by the valve base 11. As seen in FIGS. 5 and 5a and in the FIGS. 2 thru 4, the invention also includes a valve disc 15 having a central opening 16 therethrough. Disc 15 is made as thin as possible commensurate with needed strength so as to minimize the mass involved. Also, the thinner disc 15 is the less obstruction it poses to blood flow when it is in an open position. The disc material may conveniently be Pyrolite, a vitrified carbon construction, and has all peripheral edges as well as the internal edges of opening 16 rounded. The outer diameter of disc 15 is slightly less than the diameter of the opening through the annular valve base 11 so as to prevent any possibility of binding or wedging. The opening 16 is of a larger diameter than the largest portion of valve guide strut 14 for similar reasons.

Valve base 11 is provided with outwardly bell-shaped openings toward opposite sides thereof as can be seen in the several figures. This curvature is generally marked 17.

Having set forth the basic elements of the construction of the present invention, the individual components will be discussed in somewhat greater detail. Valve housing 10 has extending inwardly from a peripheral inward edge thereof the disc guide strut generally designated 14. At the point of juncture of disc guide strut 14 with the valve housing, there is provided a shoulder 19 which acts as a stop for disc 15. Disc 15 is stopped on the other side of valve housing 10 to shoulder 19 by shoulder portions 21 of inflow pivots 12. Stop 19 and the shoulder 20 of outflow pivot 13 are spaced horizontally apart a distance slightly more than the thickness of the disc 15. Thus, when the disc is at the closed or rest position, it lies in a substantially horizontal plane along the axis of the annular valve base with the shoulders 19 and 21 providing stop members.

Figure 2:
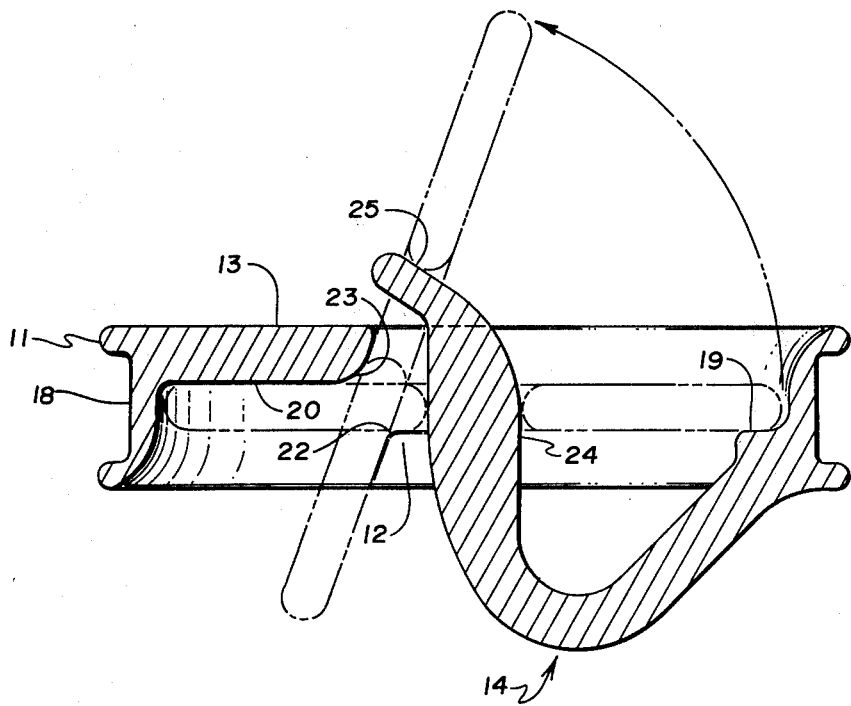
FIG. 2 is a side cross-sectional view along lines 2—2 of FIG. 1 with the valve disc shown in dotted outline in an open position.

The disc guide strut 14 is shaped generally as an S in the manner illustrated in the FIG. 2. It projects downwardly from the interior wall of valve base 11 at a substantial angle and then, as it nears the axis of the valve base, makes an S-shaped curve to pass axially through the center of valve base 11. After passing through the central portions of valve base 11, it then turns again to terminate in a short section to complete the S-shape. More specifically, the disc guide strut at the point that it departs from the valve base rim has a generally oval or ellipsoidal cross-section until it passes through the first curve of the S. At this point, it thickens gradually as shown until the central portion 24 is round and of a diameter closely approximating the diameter of the opening 16 in disc 15. This is accomplished through a gradual tapering outwardly of the guide strut. The guide strut proceeds axially through the center of the valve base and is then gradually tapered again to a smaller dimension which may be circular or of oval or ellipsoidal cross-section, and the second S-shaped portion is produced which may be a straight line section over a short distance until the end of the guide strut is reached. This latter portion functions to restrain the disc from coming free of the assembly and also permits by its narrowed cross-section movement of the valve disc in a direction outwardly away from the valve base to present less obstruction to flow of blood through the central orifice of the valve base.

The outflow pivot 13, as already indicated, has a horizontal shoulder surface 20. The cross-section of member 13 is an oval or ellipsoidal shape with the major axis in the direction of blood flow. The outflow pivot 13 extends a substantial distance into the interior of the opening in the valve base. The central internal lower surface of member 13 (designated 23) is curved with a gradual radius to provide the pivot point for the valve disc 15 as it goes into the open position. The central-most edge of member 13 is sloped to provide an angle of about 70°-75° to the axis of the valve base axis, which angular surface combines with the inflow pivots 12 and determines the maximum ultimate angle that valve disc 15 will assume in the open position.

The inflow pivots 12 extend inwardly into the inner portion of the valve base 11 along a chordal axis as shown. The two pivots are substantially identical to one another being mirror images of one another. They are integral with the ring 11 so as to provide structural integrity. Members 12 are provided with a rounded edge portion 22 which acts as the pivot point for the disc during the inflow r closing stage of valve operation.

OPERATION OF THE VALVE

In the closed position, the plane of the valve disc 15 is parallel to the plane of the valve base 11. In this position, the disc 15 resets on the two inflow pivots 12 and on the disc stop 19 of the disc guide strut. When the pressure exerted by the blood on the inflow side of the valve exceeds the pressure exerted by the outflow side, the disc begins to open. First, it is forced downstream a very short distance until it firmly contacts the outflow pivot strut 13. Thereafter, the disc pivots about curved end 23 of member 13 while being guided by the central orifice bulge portion 24, which has already been noted, tapers gradually into the final S-shaped free end portion of the guide strut 14. It should be noted that the sole pivot point is the tip of member 13 which in cooperation with the guide strut permits movement of the disc 15 in the manner indicated in the drawings. Initially, this motion is to pivot the valve disc 15 and ultimately as the valve disc 15 goes through its motion it is also displaced due to the narrowing of the guide strut in a direction outwardly away from the valve base in a downstream direction. In the solid line open position shown in FIG. 2, the disc 15 is shown in the full open but descended position. Assuming blood flow were in the outward direction, the disc 15 would move away from valve base 11 the distance equal to the difference between opening 16 and the diameter of tip 25. The maximum ultimate opening of the valve disc 15 is approximately 70°-75° to the original horizontal axis. Inflow pivots 12 also furnish a stop for the pivoting of disc 15 as the maximum angle of 70°-75° is attained.

The initial pivot point (or chordal pivot axis) is located on the outflow pivot strut and is about ¼ of the orifice diameter measured from the orifice interior walls. As a result of this location of the initial chordal pivot axis, the great majority of the pressure against the inflow side of the disc acts to force it open while the remainder acts to keep the disc closed. Therefore, the disc pivots open almost instantaneously.

During the pivoting open event, the disc exhibits three additional movements. First, the disc moves toward the center or central axis of the orifice. Second, the disc is allowed to move downstream slightly by an amount determined by the design of the free end 25 of the disc guide strut. Finally, the disc is free to rotate at any stage about its own central axis.

It should be noted that in the completely open position the disc is angled such that a minimal interference with the flow of blood is provided commensurate with the rapid functioning of the valve in a closing mode.

The closing of the valve is brought about when the pressure on the outflow side is greater than the pressure on the inflow side. When this occurs, blood begins to flow back through the valve and forces the disc into the closed position. The disc is first carried back into the orifice a small distance as allowed by the disc guide strut end 25. The motion of the disc is also restrained by encountering of the circumferential edge of the disc with interior wall portions of the valve annulus and the two inflow pivots. The valve disc then commences to pivot as permitted by the inflow pivots and as determined by the guide strut which projects through the opening 16. When approximately 20° from the closed position, the orifice-bulge 24 of the disc guide strut 14 causes the disc to lose contact with the sides of the annular valve base. Throughout the remaining pivot closing event, the disc pivots on the curved surface of the inflow pivot that projects directly into the orifice.

It can thus be appreciated that due to the many constructional features described above that an improved heart valve is provided. First, there is only a single outflow pivot point rather than the dual outflow pivots of many of the devices of the prior art. This reduces substantially the possibilities of a stagnation area for blood occurring with the obvious disadvantages of such stagnation areas. Throughout the entire movement of the disc, there is no point at which the disc is in a wedging position and thus the attendant problems that occur with wedging, such as stagnation and localized wear on the disc parts, is reduced. Likewise, the restriction against rotation of disc 15 is minimized so that uniform wear is likely to take place throughout the disc rather than any localized wear.

What is claimed is:

1. A heart valve for controlling the flow of blood comprising:
   a. a valve base of a generally annular configuration defining a circular opening therethrough, said valve base having an outflow side and an inflow said and an interior wall;
   b. inflow pivot members extending inwardly from said wall into said opening along a chordal axis towards one another and in a first plane generally parellel to the plane of said valve base, said inflow pivots being spaced towards the inflow side of said valve base;
   c. a single outflow pivot member extending radially into said opening from said wall and perpendicular to the chordal axis of said inflow pivot members, said outflow pivot member being generally in a second plane parallel to the plane of said valve base with the interior surface thereof spaced in the direction of the axis of said valve base from the interior surface of said inflow pivot members;
   d. a disc guide strut projecting generally inwardly from said wall towards the center of said valve base opening in a third plane intersecting the axis of said valve base opening and of the outflow pivot, said strut defining an S-shaped curve extending diagonally upstream out of said valve base and curving back to pass axially through the center of said opening and then curving diagonally downstream of said valve base to terminate in a free end;
   e. a valve disc of circular shape having a diameter slightly smaller than said opening, said valve disc defining an axial orifice therethrough of a diameter slightly larger than the diameter of said guide strut, said valve disc being mounted in said valve base with said guide strut extending through said orifice and being positioned when in the closed mode intermediate said inflow pivots and said single outflow pivot; and, f. a valve disc stop shoulder extending inwardly from said wall on the side of said opening opposite said outflow pivot, said shoulder being in the first plane so that said valve disc in the closed position is in the plane of said valve base.

2. A heart valve in accordance with claim 1 wherein said stop shoulder is formed by the juncture of said disc guide strut with said wall.

3. A heart valve in accordance with claim 1 wherein the interior inflow edge of said outflow pivot member is curved to facilitate pivotal movement of said valve disc to the open position and has a sloped surface at about 70°–75° to the plane of said valve base which defines with said inflow pivots the maximum open angle of said valve disc.

4. A heart valve in accordance with claim 1 wherein said guide strut has the portion which passes axially through said opening of a circular shape and a larger cross-section than the balance of said guide strut with the larger portion tapering smoothly to the smaller portions.

5. A heart valve in accordance with claim 3 wherein said outflow pivot member has a generally ellipsoidal cross-section with the major axis in the direction of blood flow.

6. A heart valve in accordance with claim 4 wherein the portion of said guide strut between the wall and axial section has a generally ellipsoidal cross-section with the major axis in the direction of blood flow.

* * * * *

UNITED STATES PATENT AND TRADEMARK OFFICE
CERTIFICATE OF CORRECTION

PATENT NO. : 4,021,863
DATED : May 10, 1977
INVENTOR(S) : Arne Woien

It is certified that error appears in the above-identified patent and that said Letters Patent are hereby corrected as shown below:

Column 3, line 1: "mdmber" should be --member--

Column 3, line 16: "r" should be --or--

Column 3, line 26: "dow-" should be --down--

Signed and Sealed this nineteenth Day of July 1977

[SEAL]

Attest:

RUTH C. MASON
*Attesting Officer*

C. MARSHALL DANN
*Commissioner of Patents and Trademarks*